(12) United States Patent
Ha et al.

(10) Patent No.: US 11,964,044 B2
(45) Date of Patent: Apr. 23, 2024

(54) PHASE CHANGE COSMETIC COMPOSITION

(71) Applicant: Amorepacific Corporation, Seoul (KR)

(72) Inventors: Dong Wan Ha, Yongin-si (KR); Yu Jung Kim, Yongin-si (KR); Dong Won Choi, Yongin-si (KR); Yoon Kyun Hwang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 17/085,496

(22) Filed: Oct. 30, 2020

(65) Prior Publication Data
US 2021/0128449 A1   May 6, 2021

(30) Foreign Application Priority Data
Oct. 31, 2019  (KR) .................. 10-2019-0137778

(51) Int. Cl.
*A61K 8/73* (2006.01)
*A61K 8/06* (2006.01)
*A61K 8/92* (2006.01)
*A61Q 19/00* (2006.01)

(52) U.S. Cl.
CPC ............... *A61K 8/92* (2013.01); *A61K 8/062* (2013.01); *A61K 8/73* (2013.01); *A61Q 19/00* (2013.01); *A61K 2800/59* (2013.01); *A61K 2800/80* (2013.01)

(58) Field of Classification Search
None
See application file for complete search history.

(56) References Cited

U.S. PATENT DOCUMENTS

| 4,950,609 | A | * | 8/1990 | Tischer | ............... | C12N 9/96 |
| | | | | | | 435/174 |
| 5,879,414 | A | * | 3/1999 | Milazzo | ............... | A61K 8/361 |
| | | | | | | 8/525 |
| 2002/0182164 | A1 | * | 12/2002 | Bossmann | ............... | A61K 8/42 |
| | | | | | | 424/70.27 |
| 2004/0166128 | A1 | * | 8/2004 | Noel | ............... | A61K 8/06 |
| | | | | | | 424/401 |
| 2007/0185281 | A1 | * | 8/2007 | Song | ............... | A61Q 5/12 |
| | | | | | | 525/375 |
| 2011/0200666 | A1 | * | 8/2011 | Teichmuller | ............... | A61K 8/73 |
| | | | | | | 977/773 |
| 2016/0346172 | A1 | * | 12/2016 | Pistorio | ............... | A61K 8/044 |
| 2019/0091493 | A1 | * | 3/2019 | Suleiman | ............... | A61K 8/8158 |

FOREIGN PATENT DOCUMENTS

| JP | 5555074 B2 | 7/2014 |
| KR | 10-2009-0073368 A | 7/2009 |
| KR | 10-1787507 B1 | 10/2017 |
| KR | 10-1837433 B1 | 3/2018 |

OTHER PUBLICATIONS

Chemical Book, Cetyl Palmitate, https://www.chemicalbook.com/ChemicalProductProperty_EN_CB8749079.htm, obtained online Feb. 7, 2022 (Year: 2022).*

* cited by examiner

*Primary Examiner* — Jennifer A Berrios
(74) *Attorney, Agent, or Firm* — Sughrue Mion, PLLC

(57) ABSTRACT

One aspect of the present disclosure relates to a phase transfer cosmetic composition. According to the present disclosure, there can be provided a cosmetic composition which contains a wax having a melting point of 40 to 60° C. and an inulin-based surfactant, wherein the composition maintains a liquid state before applied to the skin and rubbed, and changes to a solid state when applied to the skin, can solve the problems in terms of hygiene and use because it is not used by scooping it by hand, and further, changes its phase to a solid state when applied to the skin and then rubbed, and thus, can solve the problem of dripping when applied to face or skin.

12 Claims, 2 Drawing Sheets
(2 of 2 Drawing Sheet(s) Filed in Color)

PHASE CHANGE COSMETIC COMPOSITION

TECHNICAL FIELD

Cross-Reference to Related Application

This application claims the benefit of priority from Korean Patent Application No. 10-2019-0137778 filed with the Korean Intellectual Property Office on Oct. 31, 2019, the entire content of which is hereby incorporated by reference.

One aspect of the present disclosure relates to a phase transfer cosmetic composition, and more particularly to a cosmetic composition which contains a wax having a melting point of 40 to 60° C. and an inulin-based surfactant, wherein the composition maintains a liquid state before applied to a skin and rubbed, and the phase changes to a solid or non-flowable state when applied to the skin and then rubbed.

BACKGROUND ART

In general, cosmetic compositions in liquid form have the disadvantage that they drip down immediately when applied to a face or skin, making it inconvenient to use. Since cosmetic compositions in solid form is used in the form of balm type, it must be scooped and used with fingers in order to apply to the face or skin. When the cosmetic composition in solid form is scooped and applied fingers in this way, there is a disadvantage in that it causes contamination of the container, resulting in hygiene problems, and also the composition is stained on the hands, causing the trouble of washing the hands again.

As a conventional technique for solving the problem in terms of such properties, a cosmetic composition that maintains a solid form at low temperature and transfers its phase to a liquid form after the passage of a predetermined time at the temperature of human skin has been published, but there is a disadvantage that it transfers the phase to a liquid form at the temperature of the human skin and still drips from the face or skin. Furthermore, there is inconvenience in use in that it must be stored under refrigeration before application.

Therefore, there is a need to develop a cosmetic composition that maintains a liquid form before being applied to the skin and rubbed, and transfers its phase to a solid form when applied to the skin.

DETAILED DESCRIPTION OF THE INVENTION

Technical Problem

The above disclosure has been designed to solve that above-mentioned problems, and an object of the present disclosure is to provide a cosmetic composition that maintains a liquid form before being applied to the skin and rubbed, and thus, can solve the problems in terms of hygiene and use because it is not used by scooping it with fingers, and further, transfers its phase to a solid form when applied to the skin and then rubbed, and thus, can solve the problem of dripping when applied to the face or skin.

Technical Solution

In order to achieve the above-mentioned object, one aspect of the present disclosure provides a cosmetic composition which contains a wax having a melting point of 40 to 60° C. and an inulin-based surfactant, wherein the composition maintains a liquid form before being applied to a skin and rubbed, and changes its phase to a solid or non-flowable state when being applied to the skin and then rubbed.

Advantageous Effects

According to the present disclosure, there can be provided a cosmetic composition that maintains a liquid form before being applied to the skin and rubbed, and transfers its phase to a solid or non-flowable state when applied to the skin and the rubbed, and thus, can solve the problems of hygiene and use because it is not used by scooping it by hand, and solve the problem of dripping when applied to the face or skin.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE EMBODIMENTS

Figure 1:
FIG. 1 is a view showing the phase immediately after applying the cosmetic composition of one embodiment of the present invention to a skin.

Hereinafter, the present disclosure will be described in detail with reference to examples and drawings.

The phase transfer cosmetic composition according to one aspect of the present disclosure is characterized in that it maintains a liquid state before being applied to the skin and rubbed, and transfers its phase to a solid or non-flowable state when being applied to the skin and then rubbed. The present inventors have conducted intensive research to solve: disadvantages of cosmetic compositions in liquid form, which is not easy to use because it drips immediately when applied to the face or skin, and disadvantages of cosmetic compositions in solid (either hard or soft solid) state which cause hygiene problems because it will contaminate the container when scooping by hand and applying the cosmetic composition, and which causes the hassle of washing the user's hands after applying the composition, and as a result, have found that when the cosmetic composition contains a wax having a melting point of about 40 to about 60° C. and an inulin-based surfactant as an active ingredient, it maintains a liquid form at a room temperature before being applied to the skin, and transforms to a solid state (or a non-flowable state) when being applied to the skin and then rubbed, thereby completing the present invention.

The term "liquid state" as used herein means that the composition exhibits fluidity at room temperature and has a viscosity of about 150 mPa·s or higher, and preferably about 180 mPa·s or higher, a viscosity of about 250 mPa·s or lower, and preferably about 230 mPa·s or lower, and most preferably a viscosity or about 200 mPa·s. When the viscosity is less than the above lower limit, the composition may drip down immediately after being applied to the skin, and when the viscosity exceeds the upper limit, the fluidity may decrease, making it difficult to dispense composition from the container to apply to the skin.

The cosmetic composition according to one aspect of the present disclosure provides the advantage of being hygienic since it maintains a liquid form before being applied to the skin and rubbed as described above, and thus, it is possible to apply the cosmetic composition without the necessity to scoop it with fingers. In addition, the meaning of maintaining a liquid form before the cosmetic composition according to one aspect of the present disclosure is applied to the skin and rubbed as described, of course, includes the meaning of maintaining a liquid state by exhibiting fluidity at room temperature even in a state of being stored in a container before being applied to the skin. Therefore, it provides the advantage that it can be stored in various types of containers without being necessarily used in the form of balm type. Specifically, it can be stored in various containers such as bottle type, tube type, jar type, roller-ball type, pen type, stick type, lid/stopper type, pump/dispenser type.

The term "solid state" as used herein means that the composition has no fluidity or is not flowable at room temperature, and means that when measured using a hardness meter (Sun Rheo Meter™, Compac™ CR-100D, manufactured by Sun Scientific, Mode No. 20, spindle 1.5 cm, speed 1 cm/min, penetration distance 20 mm), it has a hardness of 60 $gf/cm^2$ or higher. In an embodiment, the hardness is about 70 $gf/cm^2$ or higher, and about 100 $gf/cm^2$ or lower. In an aspect, the hardness is about 80 $gf/cm^2$ or lower, and may be about about 75 $gf/cm^2$.

In the present disclosure, the wax having a melting point of about 40 to about 60° C. is an active ingredient that provides a phase transfer effect together with the inulin-based surfactant, and a low melting point wax having a melting point of about 50° C. or lower and a high melting point wax having a melting point of about 70° C. or higher can be mixed and used. A wax ester may be preferably used.

The low melting point wax may include hydrogenated olive oil lauryl esters, *Oryza sativa*(rice) bran wax, Astrocayum *Murumuru* Seed Butter, and the like, and the high melting point wax may include sunflower seed wax, bees wax, candelilla wax, carnauba wax, jojoba seed wax, and jasmine flower wax, Ozokerite, synthetic wax, and the like.

Examples of the wax ester may include C16-C40-alkyl stearate, C20-C40-alkyl stearate, C20-C40-dialkyl esters of dimer acids, C18-C38-alkyl hydroxystearoylstearate, C20-C40-alkyl erucate, C30-C50-alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate, behenyl behenate, or the like.

The wax component can improve the stability of the cosmetic composition within the melting point range of about 40 to about 60° C. and can provide the phase transfer effect intended by the present disclosure. As the wax having the above melting point range and exhibiting the above effect, it is most preferable to use a cetyl ester.

In one aspect of the present disclosure, the inulin-based surfactant is an active ingredient that provides a phase transfer effect together with the wax having a melting point of about 40 to about 60° C., and is preferably at least one selected from the group consisting of inulin, stearoyl inulin, inulin lauryl carbamate and palmitoyl inulin. As the inulin-based surfactant having the above melting point range and exhibiting the above effect, it is most preferable to use inulin lauryl carbamate, which prevents Oswald ripening phenomenon in which particles having a relatively small size continue to decrease, and large particles grow larger and eventually the smaller particles disappear.

At this time, the content of the wax may be about 15% by weight or more. In an embodiment, the wax content may be about 17% by weight, and about 20% by weight or less, or about 19% by weight or less based on the total weight of the composition. In an embodiment, the content of the wax is about 18% by weight based on the total weight of the composition. The content of the inulin-based surfactant is about 0.125% by weight or more, or about 0.3% by weight or more and 0.5% by weight or less based on the total weight of the composition. In an embodiment, the content of the inulin-based surfactant is about 0.5% by weight based on the total weight of the composition. In particular, within the above content range, it is possible to provide the phase transfer effect intended by the present disclosure.

The formulation of the cosmetic composition according to one embodiment of the present disclosure is preferably an oil-in-water formulation in which the inner phase is an oil phase and the external phase is an aqueous phase. In the cosmetic composition according to one embodiment of the present disclosure, it is preferable that the wax is contained in the oil phase, and the inulin-based surfactant is contained in the aqueous phase. In this case, the content of the oil phase may be about 16.5% by weight or more based on the total weight of the composition, and about 49.5% by weight or less based on the total weight of the composition. Specifically, in an embodiment, it is not less than about 16.5% by weight, but more than about 16.5% by weight, and not more than about 49.5% by weight, but less than about 49.5% by weight. More specifically, it is about 20% by weight or more, or about 25% by weight or more, or about 30% by weight or more, and about 45% by weight or less, about 40% by weight or less, about 35% by weight or less, based on the total weight of the composition.

The content ratio of the oil phase and the water phase is about 1:1 to 3, about 1:1.5 to 2.5, or about 1:2 to 2.3 based on the weight. Within the above content range and within the above content ratio range, it is possible to provide a phase transfer effect that is particularly desired by the present disclosure.

The term "about" as used herein includes the specific value or end-point referred to and includes ranges within ±10%, ±9%, ±8%, ±7%, ±6%, ±5%, ±4%, ±3%, or ±2% variances.

The oil phase may contain an oil component, and the oil component used may be various oils known in the art. Specifically, hydrocarbon-based oils such as hexadecane and paraffin oil, ester-based synthetic oils such as isopropyl myristate, silicone oils such as dimethicone and cyclomethicone, animal and vegetable oils such as corn oil, soybean oil, avocado oil, sesame oil, jojoba oil, sunflower oil, nut oil, squalene and fish oil, oil components such as ethoxylated alkyl ether oil and propoxylated alkyl ether oil, and the like can be used.

In addition, the oil phase may further contain a lipid component, and the lipid component may include ceramide, cholesterol, stearic acid, or the like. The ceramide may be a natural ceramide or a synthetic ceramide, and the synthetic ceramides also include pseudoceramides. As the inulin-based surfactant exhibiting the above effect, it is most preferred to use hydroxypropyl bispalmitamide MEA (N-[3-[hexadecanoyl(2-hydroxyethyl)amino]-2-hydroxypropyl]-N-(2-hydroxyethyl)hexadecanamide), which is a kind of the pseudoceramide.

According to a preferred embodiment of the present disclosure, the phase transfer cosmetic composition according to one aspect of the present disclosure is prepared through a high pressure emulsification method. Specifically, the phase transfer cosmetic composition is prepared through the steps of: preparing an oil phase containing a wax having a melting point of about 40 to about 60° C., preparing an aqueous phase containing an inulin-based surfactant, mixing after adding the oil phase to the water phase so that the content ratio of the oil phase and the water phase part is about 1:1 to 3 on the weight basis, and subjecting the mixture obtained by the mixing to high-pressure emulsification at a pressure of 500 to 1500 bar.

In addition to the above ingredients, the cosmetic composition may contain a moisturizing agent, an anti-inflammatory agent, an antibacterial agent, an antifungal agent, an UV blocking agent, an UV absorber, antibiotics, or the like. The moisturizing agent may include glycerin, 1,3-butylene glycol, dipropylene glycol, propylene glycol, sorbitol, a natural extract, or the like conventionally used for cosmetics. Further, the cosmetic composition may include conventional adjuvants such as stabilizers, solubilizers, vitamins, dyes, pigments, and fragrances conventionally used in the field of a cosmetic composition.

EXAMPLES

Hereinafter, the present disclosure will be described in detail by way of examples. However, the following examples are merely examples for assisting the overall understanding of the present disclosure, and the contents of the present disclosure are not limited to the examples.

<Preparation Example 1> Preparation of the Composition

The compositions of Example 1, Comparative Example 1 (formulation in which the content of wax is less than the preferred range), Comparative Example 2 (formulation in which the content of wax exceeds the preferred range), Comparative Example 3 (formulation in which the content of the oil phase is less than the preferred range), Comparative Example 4 (formulation in which the content of the oil phase exceeds the preferred range), Comparative Example 5 (formulation containing carnauba wax, not cetyl ester as wax), Comparative Example 6 (formulation containing PPG-13-decyltetradeceth-24, not inulin lauryl carbamate as surfactant), Comparative Example 7 (formulation in which the content of inulin lauryl carbamate is less than the preferred range) and Comparative Example 8 (formulation in which the content of inulin lauryl carbamate exceeds the preferred range) were prepared according to the components and contents of Table 1 below (unit: wt %).

The method of preparing the composition is as follows. The raw materials 1 to 4 in Table 1 were mixed and then heated to 70° C. to prepare an oil phase. The raw materials 5 to 8 in Table 1 were mixed and then heated to 70° C. to prepare an aqueous phase. The oil phase was gradually added to the water phase and then stirred to make it uniform, which was subjected to first emulsification. The first emulsion was passed through a high-pressure homogenizer three times at a pressure of 1,000 bar to prepare the compositions of Example 1 and Comparative Examples 1 to 8.

<Experimental Example 1> Evaluation of the Phase of the Composition

First, in the case of Comparative Example 2, which is a formulation in which the content of the wax exceeds the preferred range, it was confirmed that the stability is not so good to the extent that the particles can be visually observed from the beginning, and it is impossible to prepare a stable composition by the above preparation method. In the case of Comparative Example 5, which is a formulation containing carnauba wax, not cetyl ester as a wax, it was confirmed that it was impossible to prepare a stable liquid composition since it was prepared in a solid form from the beginning.

In the case of Comparative Example 3, which is a formulation in which the content of the oil phase is less than the preferred range, it is prepared in the form of a water skin rather than an emulsion, and in the case of rubbing after be applied to the skin, there was no tendency to be precipitated as a solid, which is the characteristic of the present disclosure.

In the case of Comparative Example 4, which is a formulation in which the content of the oil phase exceeds the preferred range, it is prepared in a sticky form with a higher viscosity than a soft emulsion form, it showed a tendency to be precipitated in a solid form before being applied to the skin.

In the case of Comparative Example 6, which is a formulation containing PPG-13-decyltetradeceth-24, not inulin lauryl carbamate as a surfactant, the peculiar phase transfer feeling is decreased and the stability also tended to decrease.

In the case of Comparative Example 7, which is a formulation in which the content of inulin lauryl carbamate is less than the preferred range, it showed a tendency to be less stable, and in the case of Comparative Example 8, which is a formulation in which the content of inulin lauryl

TABLE 1

| Component | Example 1 | Comparative Example 1 | 2 | 3 | 4 | 5 | 6 | 7 | 8 |
|---|---|---|---|---|---|---|---|---|---|
| 1. cetyl ester | 18 | 12 | 24 | 9 | 27 | — | 18 | 18 | 18 |
| 1. carnauba wax | — | — | — | — | — | 18 | — | — | — |
| 2. polyglyceryl-3 methylglucose distearate | 2 | 2 | 2 | 1 | 3 | 2 | 2 | 2 | 2 |
| 3. hydroxy propyl bispalmitamid MEA | 1 | 1 | 1 | 0.5 | 1.5 | 1 | 1 | 1 | 1 |
| 4. natural oil | 12 | 12 | 12 | 6 | 18 | 12 | 12 | 12 | 12 |
| 5. deionized water | To 100 | To 100 | To 100 | To 100 | To 100 | To 100 | To 100 | To 100 | To 100 |
| 6. Inulin lauryl carbamate | 0.5 | 0.5 | 0.5 | 0.5 | 0.5 | 0.5 | — | 0.1 | 1 |
| 6. PPG-13-decyltetradeceth-24 | — | — | — | — | — | — | 0.5 | — | — |
| 7. glycerin | 4 | 4 | 4 | 4 | 4 | 4 | 4 | 4 | 4 |
| 8. PERMANDIOL ® (propanediol) | 15 | 15 | 15 | 15 | 15 | 15 | 15 | 15 | 15 | carbamate exceeds the preferred range, the peculiar phase transfer feeling tended to fall.

On the contrary, in the case of Example 1, it was prepared in the form of an emulsion as shown in FIG. 1 before being applied to the skin and rubbed after preparation.

Figure 2:
FIG. 2 is a view showing the phase when rubbing after applying the cosmetic composition of one embodiment of the present invention to a skin.

In the case of rubbing after application to the skin, it showed the tendency to be precipitated in a solid form as shown in FIG. 2.

<Experimental Example 1> Evaluation of the Immediate Phase Transfer Feeling of the Composition For the prepared composition, the immediate phase transfer feeling was expressed as the average value of the value evaluated by conducting a feeling test through a professional panel (5 point scale).
<Evaluation Criteria on a 5-Point Scale>
5 points: agree very much 4 points: agree 3 points: moderate
2 points: don't agree 1 point: don't think so at all

TABLE 2

| Evaluation item | Example 1 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Phase transfer feeling | 5 | 3 | Cannot be manufactured | 2 | 2 | Cannot be manufactured | 1 | 1 | 1 |

From the results of Table 2, it can be seen that in the case of Example 1, the immediate phase transfer feeling is excellent, and in particular, in the case of Comparative Example 1, which is a formulation in which the content of the wax is less than the preferred range, the phase transfer feeling is lowered. In the case of Comparative Example 4, which is a formulation in which the content of the oily part exceeds the preferred range, the film feeling was excessively severe when rubbing after application to the skin, resulting in a decrease in the phase transfer feeling. In addition, in the case of Comparative Examples 3 and 6 to 8, it was found that the phase transfer feeling was greatly reduced.

Although the present disclosure has been described in connection with the above-mentioned preferred embodiments, various modifications or variations can be made to the disclosure without departing from the spirit and scope of the invention. Therefore, such modifications or variations will be included in the appended claims as long as they fall within the gist of the present disclosure.

The invention claimed is:

1. A phase change cosmetic composition which contains a cetyl ester wax and an inulin-based surfactant,
   wherein the inulin-based surfactant is inulin lauryl carbamate,
   wherein the composition is an oil-in-water formulation in which an inner phase is an oil phase and an external phase is an aqueous phase, and the cetyl ester wax is contained in the oil phase, and the inulin-based surfactant is contained in the aqueous phase,
   wherein a content of the cetyl ester wax is 17 to 20% by weight based on a total weight of the composition, and a content of the inulin-based surfactant is 0.125 to 0.5% by weight based on the total weight of the composition, and
   wherein the composition maintains a liquid state at a room temperature before applied to a skin and rubbed, and changes to a solid state when applied to the skin and then rubbed.

2. The phase change cosmetic composition of claim 1, wherein the composition maintains a liquid state having a viscosity of 150 to 250 mPa·s before applied to the skin and rubbed, and changes to a solid state having a hardness of 60 to 100 gf/cm$^2$ when applied to the skin and then rubbed.

3. The phase change cosmetic composition of claim 1, wherein a content of the cetyl ester wax is 17 to 19% by weight based on the total weight of the composition, and a content of the inulin-based surfactant is 0.3 to 0.5% by weight based on the total weight of the composition.

4. The phase change cosmetic composition of claim 1, wherein a content of the oil phase is about 16.5 to about 49.5% by weight based on the total weight of the composition.

5. The phase transfer cosmetic composition of claim 1, wherein a weight ratio between a weight of the oil phase and a weight of the water phase is about 1:1 to about 1:3.

6. A method for preparing the phase change cosmetic composition of claim 1, comprising the steps of:
   preparing an oil phase containing a cetyl ester wax,
   preparing an aqueous phase containing an inulin-based surfactant,
   mixing the oil phase with the water phase so that a weight ratio between a weight of the oil phase and a weight of the water phase is about 1:1 to about 1:3 to prepare a mixture, and
   subjecting the mixture to an emulsification at a pressure of about 500 to about 1500 bar,
   wherein the inulin-based surfactant is inulin lauryl carbamate
   wherein a content of the cetyl ester wax is 17 to 20% by weight based on the total weight of the composition, and a content of the inulin-based surfactant is 0.125 to 0.5% by weight based on the total weight of the composition,
   wherein the composition is an oil-in-water formulation in which an inner phase is an oil phase and an external phase is an aqueous phase, and the cetyl ester wax is contained in the oil phase, and the inulin-based surfactant is contained in the aqueous phase, and
   wherein the composition maintains a liquid state before being applied to a skin and rubbed, and changes to a solid state when applied to the skin and then rubbed.

7. The method of claim 6, wherein the composition maintains a liquid state having a viscosity of 150 to 250 mPa·s before being applied to the skin and rubbed, and changes to a solid state having a hardness of 60 to 100 gf/cm$^2$ when being applied to the skin and then rubbed.

8. The method of claim 6, wherein a content of the cetyl ester wax is 17 to 19% by weight based on the total weight of the composition, and a content of the inulin-based surfactant is 0.3 to 0.5% by weight based on the total weight of the composition.

9. The method of claim 6, wherein a content of the oil phase is about 16.5 to about 49.5% by weight based on the total weight of the composition.

10. The method of claim 6, wherein a weight ratio between a weight of the oil phase and a weight of the water phase is about 1:1 to about 1:3.

11. The phase change cosmetic composition of claim 1, wherein a content of the cetyl ester wax is 18 to 20% by weight based on the total weight of the composition.

12. The method of claim 6, wherein a content of the cetyl ester wax is 18 to 20% by weight based on the total weight of the composition.

\* \* \* \* \*